(12) United States Patent
Tu et al.

(10) Patent No.: US 7,574,931 B2
(45) Date of Patent: Aug. 18, 2009

(54) QUANTITATIVE SAMPLING DEVICE

(76) Inventors: Shing-Huang Tu, No. 23, Alley 18, Lane 177, Chongcing Street, Bade City, Taoyuan County (TW); Ling-Yuan Chou, 4F, No.92, Wen-Hwa Street, Hsinchu (TW); Su-Chen Hsu, 2F, No.9, 206 lane, hua-xin street, zhong-ho city, Taipei county (TW)

( * ) Notice: Subject to any disclaimer, the term of this patent is extended or adjusted under 35 U.S.C. 154(b) by 446 days.

(21) Appl. No.: 11/486,208

(22) Filed: Jul. 14, 2006

(65) Prior Publication Data
US 2008/0011105 A1    Jan. 17, 2008

(51) Int. Cl.
*G01N 1/00*    (2006.01)
(52) U.S. Cl. .................................................. 73/864.72
(58) Field of Classification Search .............. 73/864.72; 435/309.3
See application file for complete search history.

(56) References Cited

U.S. PATENT DOCUMENTS

| | | | | |
|---|---|---|---|---|
| 4,115,200 | A | * | 9/1978 | Anderson ................ 435/286.4 |
| 4,801,547 | A | * | 1/1989 | Rosenberg ............... 435/309.3 |
| 6,245,559 | B1 | * | 6/2001 | DeVaughn et al. ...... 435/309.3 |

OTHER PUBLICATIONS

Abdulganieva et al, "Nutrient medium for isolation of hemocultures", Dec. 12, 2005.*

* cited by examiner

*Primary Examiner*—Robert R Raevis
(74) *Attorney, Agent, or Firm*—Muncy, Geissler, Olds & Lowe, PLLC

(57) ABSTRACT

A quantitative sampling device comprises a sampling part and a case; the sampling part further has a sampling loop with a predetermined size for sampling a fixed amount of an liquid sample; and the case includes a buffer solution with a predetermined volume, the sampling part is adapted for slidable communication within the case, and the liquid sample may mix with the buffer solution after the sampling part propelled in to get a diluted solution.

9 Claims, 3 Drawing Sheets

US 7,574,931 B2

QUANTITATIVE SAMPLING DEVICE

BACKGROUND OF THE INVENTION (1) Field of the Invention

The present invention relates to a sampling device, especially to a sampling device which could sample quantitatively and the method thereof.

(2) Description of the Prior Art

Point of care testing (POCT) is testing performed by or on behalf of a medical practitioner at the time of consultation, allowing the results to be used to make immediate, informed decisions about patient care.

The need for simple methods to determine the chemical and biological constituents in body fluids has increased as POCT has gained in popularity. For instance, liver and renal function test, blood glucose administering or HDL/LDL detection are common to practice through POCT.

There is an increasing trend, however, toward POCT and even in-home testing. One of the benefits of this trend is to minimize the turnaround time from when a sample is taken to being able to take action based on the test results. Other advantage of POCT is easy to be performed at home environment for patients to monitor chronic disease themselves.

A common application is the self monitoring of blood glucose concentrations by patients with diabetes. These patients frequently administer insulin or take other therapeutic actions based on the test results. As testing is generally recommended multiple times daily and may occur in any setting, an easy to use and relatively inexpensive method to accomplish this task is required.

However, the procedures during POCT may be performed by a practitioner who is not a professional, hence increasing the risk of contaminating analysis samples.

For instance, most blood related tests need isolation pretreatments for isolating blood cells from plasma before analysis in apparatus, this procedure may be performed through manual operation such as adding organic solvent and centrifugation, hence contaminate phenomenon might occurred; moreover, some tests need quantitative analysis, and manual pretreatment through a non-professional may cause error during sampling processes.

Therefore, given the current pressures on improving the efficiency of POCT, inexpensive, easy to performance and high accuracy alternatives to expensive and complicated analysis methods would be welcomed.

SUMMARY OF THE INVENTION

The object of the present invention is to provide a sampling device which could be used for sample quantitatively.

Another object of the present invention is to provide a quantitative sampling device which could be simplify pretreatment procedures and decrease contamination due by manual operation.

According to the present invention, a quantitative sampling device comprises a sampling part and a case; the sampling part further has a sampling loop with a predetermined size for sampling a fixed amount of an liquid sample; and the case includes a buffer solution with a predetermined volume, the sampling part is adapted for slidable communication within the case, and the liquid sample may mix with the buffer solution after the sampling part propelled in to get a diluted solution.

There's further a filter membrane coupled to the case, the diluted solution passes through the filter membrane due by expelling pressure while the sampling part further propelled into the case to get a separated sample. The output part is coupled to the filter membrane to output the separated sample.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1A:
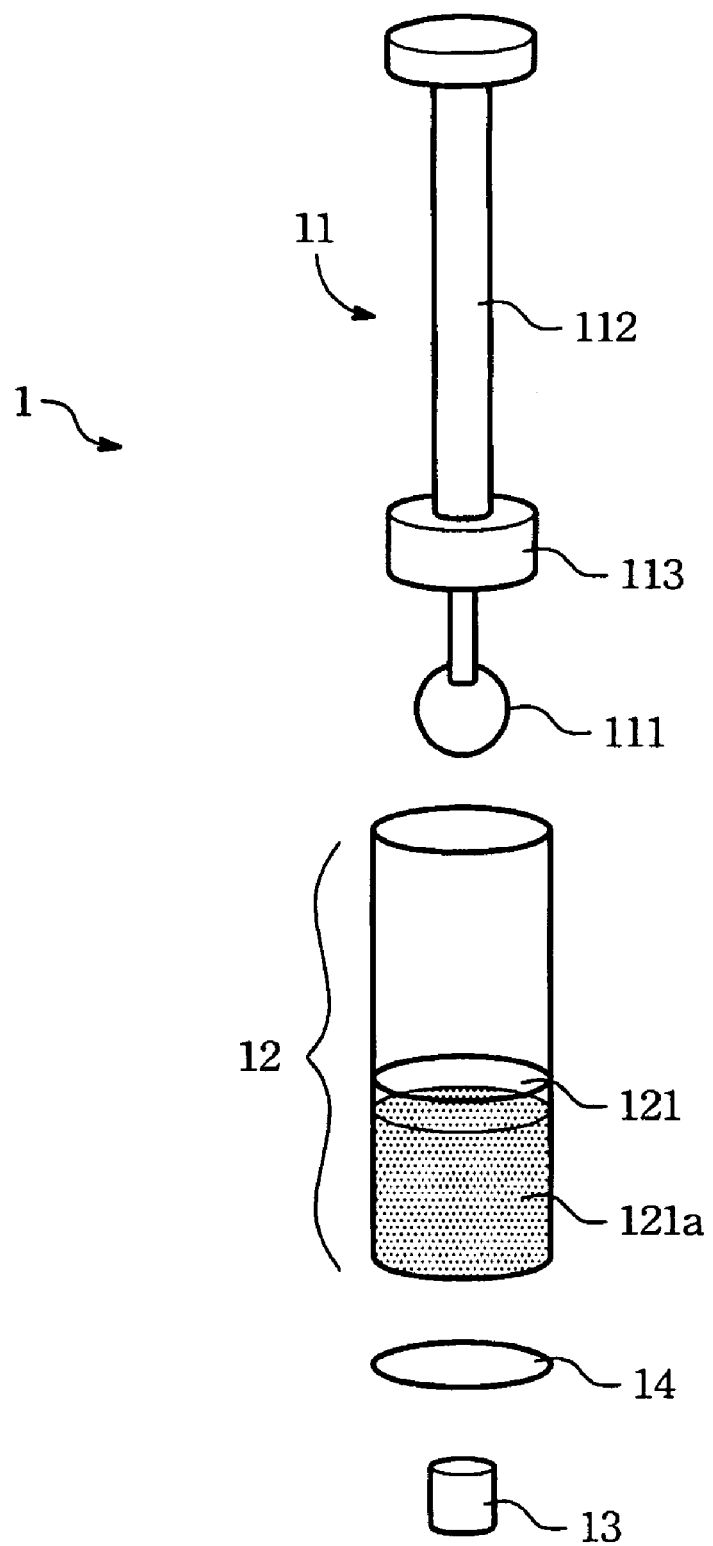
FIG. 1A shows a quantitative sampling device of the first embodiment in accordance with the present invention.

Please refer of FIG. 1A, which shows a quantitative sampling device of the first embodiment in accordance with the present invention. All the contents and elements in the present invention are sterilized in advance before using. The quantitative sampling device 1 comprises a sampling part 11, a case 12 and a output part 13; the sampling part 11 is adapted for slidable communication within the case 12. As FIG. 1A shows, the sampling part 11 comprises a sampling loop 111, the sampling loop 111 has a predetermined size (diameter) for sampling a fixed amount of a liquid sample. Applied in POCT, liquid samples could be varied, blood sample, bodily fluid sample (for instance, cerebrospinal fluid) or other liquid samples which are easy sampling by the sampling loop due by surface tension could be sampled quantitatively herein. Additionally, the sampling loop 111 of the first embodiment is a metal loop having a diameter about 2-8 mm, however, the material and the size of the sampling loop are variable in different embodiments to suit different needing of different sample.

The case 12 includes a buffer solution with a predetermined volume, while the sampling part 11 is propelled into the case 12, the liquid sample on the sampling loop 111 will mix with the buffer solution within the case 12 to get a diluted solution. Because the size of the sampling loop is fixed, and the volume of the buffer solution is fixed too, hence different sampling procedures could almost results diluted solution having almost the same concentration and volume. Therefore decreasing sampling errors due by different practitioners mentioned in the background.

There's a filter membrane 14 coupled to an opening end of the case 12 for isolating the diluted solution to get an separated sample. The output part 13 is coupled to the filter membrane 14 for outputting the separated sample.

The sampling part 11 may works as a plunger, comprises the sampling loop 111 and a bar 112 having a piston ring 113, the piston ring 113 with a bit elasticity provides the sampling part 11 tight fitted in the case 12 while being propelled in.

In some embodiments, the case 12 further comprises a sealed housing 121 for stuffing with the buffer solution 121a in advance, and the sealed housing 121 breaks due by the expelling pressure while the sampling part 11 propelling along the case 12, and then the buffer solution 121a may mix with the liquid sample that on the sampling loop 111.

Figure 1B:
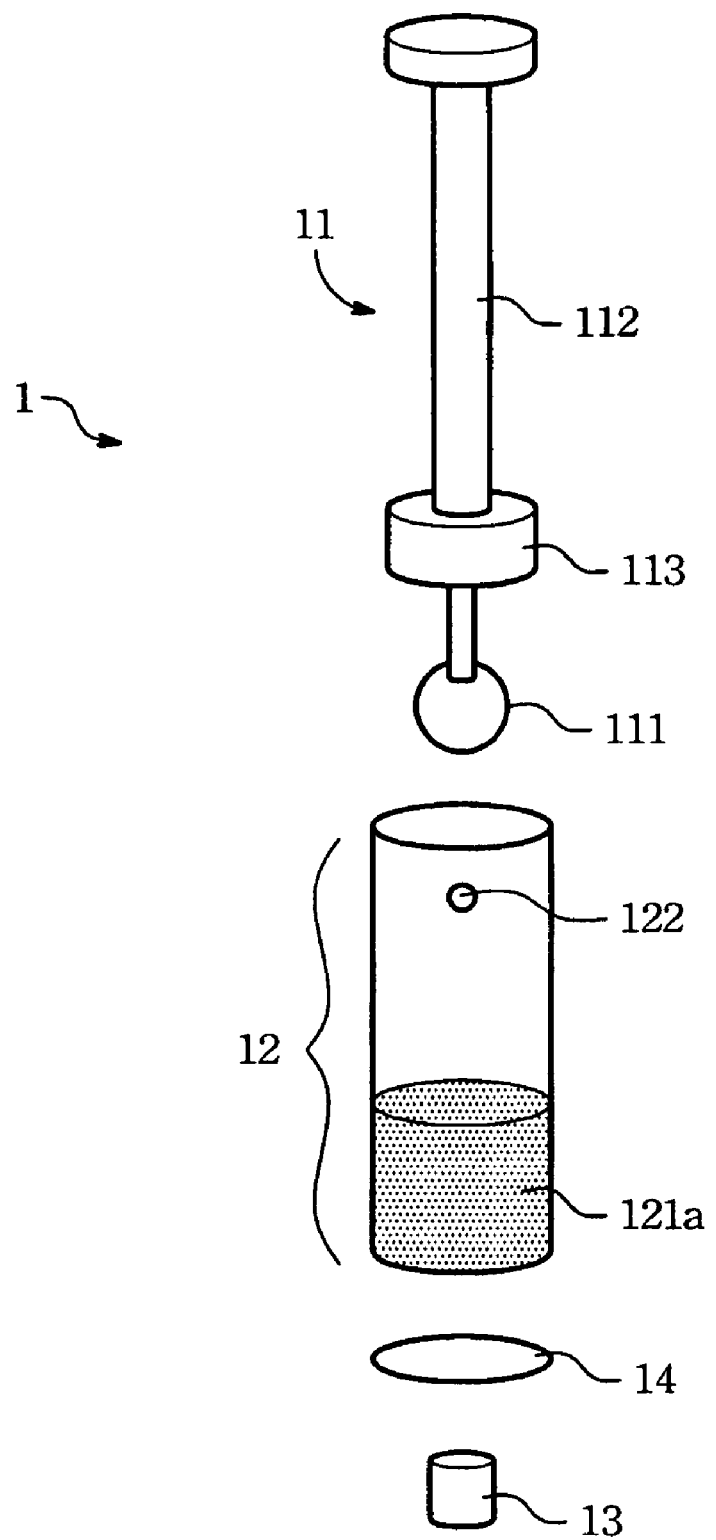
FIG. 1B shows a quantitative sampling device of another embodiment in accordance with the present invention.

In other embodiments, the sealed housing 121 is not necessary, please refer of FIG. 1B, the case 12 is stuffed with the buffer solution 121a in advance, and the case 12 comprises a gas hole 122 as FIG. 1B shows. While the sampling part propelling along the case 12, the expelling pressure exhausted from the gas hole 122 to avoid exhaust of the buffer solution 121a from the output part 13 in the beginning of the propelling.

In conventional sampling procedures, especially for microanalysis, a pipet is needed for sampling little amount of liquid sample. Comparing to conventional procedures, the sampling loop 111 is used to quantitatively sample the liquid sample, the sampling procedure is less-cost and much convenient. Moreover, the mix treatment of the liquid sample is finished in the sterile case 12, hence solving the contamination problems due by manual operation.

Different liquid samples need different pretreatment procedures before analysis in various analysis apparatuses. A blood glucose monitoring test only needs analyzing a whole blood sample directly, however, most blood test need a pretreatment procedure to dilute the blood sample and then to rid of blood cell before analyzing in analysis apparatuses. The filter membrane 14 works as a role to separate the blood cells from plasma according to the pororosity thereof. The pore size of the filter membrane is not restricted herein, the pore size is variable in response to different liquid samples. The separated sample from the output part outputs to corresponding analysis apparatus, the shape and size of the output part may vary according to different analysis apparatuses, in some embodiments, the output part could be a needle shaped to drip the separated sample into an analysis apparatus.

In the present invention, the quantitative sampling, sample dilution and separation are all finished within the quantitative sampling device of the present invention, not only the pretreatment procedures are simplified compared to conventional procedures, the risks of errors due by manual operation are also minimized.

The pretreatment method of a liquid sample using the quantitative sampling device disclosed in the present invention comprises the following steps:

Step 201: quantitatively sampling the liquid sample through the sampling loop, the sampling loop having a predetermined size to quantitatively sample the liquid sample through surface tension, the liquid samples could be blood, bodily fluids or other samples having liquid form;

Step 202: propelling the sampling loop into the case;

Step 203: repeatedly mixing the buffer solution and the liquid sample to get a diluted solution through manual shaking or machine shaking, herein the buffer solution could be stuffed within the case in advance (refer to the first embodiment) or stuffed within the sampling part (refer to a second embodiment described later), no matter where the buffer solution is stuffed in advance, the mix procedure happened after the sampling part propelled into the case;

Step 204: further propelling the sampling part to force the diluted solution passes through the filter membrane for isolating the diluted solution to get an separated sample, the filter membrane isolates passed samples according to different pore sizes thereof.

As the said, position of the buffer solution is not restricted in the present invention, a location that satisfies mixing the buffer solution and the liquid sample after the sampling part propelled into the case could be applied in the present invention.

Figure 2:
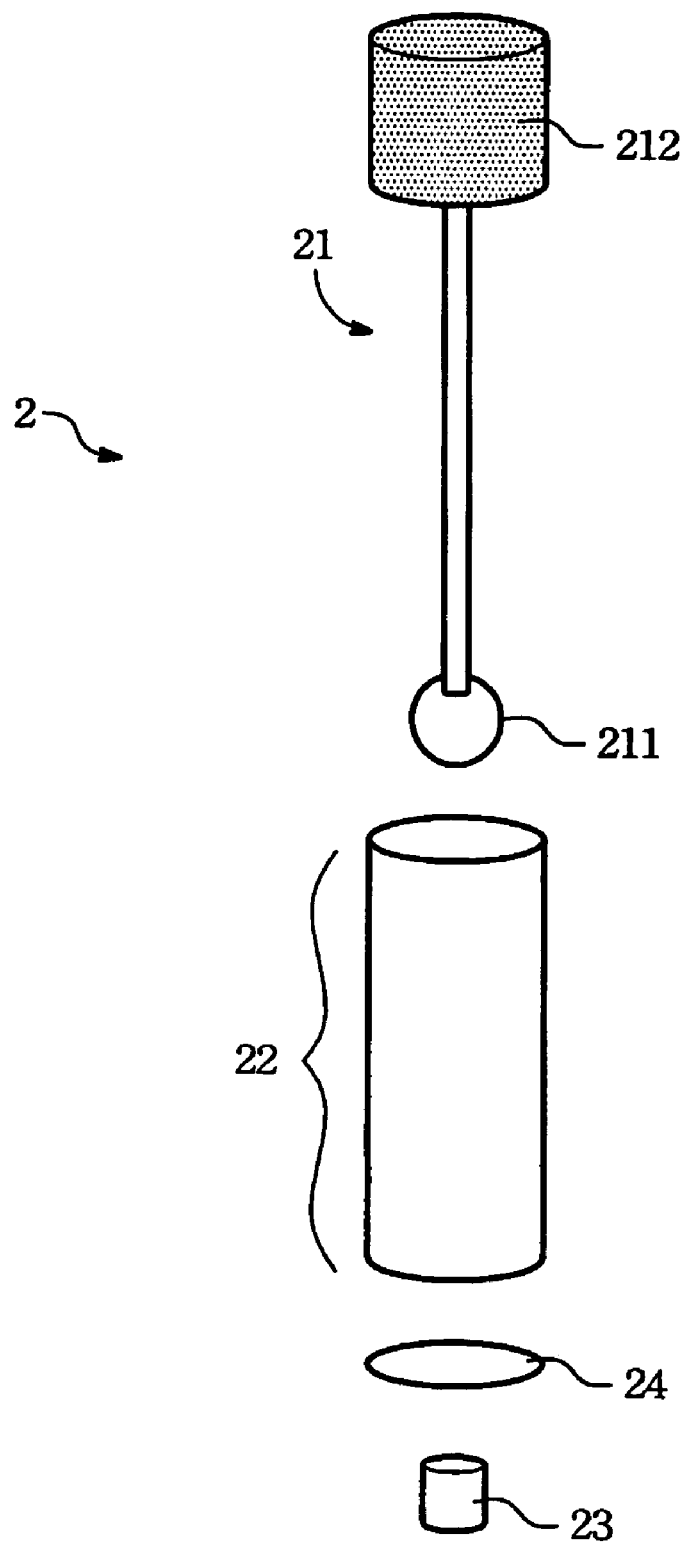
FIG. 2 is a quantitative sampling device of the third embodiment in accordance with the present invention.

Please refer to FIG. 2, which is a quantitative sampling device of the third embodiment in accordance with the present invention. The quantitative sampling device 2 comprises a sampling part 21, a case 22 and an output part 23. The sampling part 21 further comprises a sampling loop and includes a buffer solution with a predetermined volume. The difference between the third embodiment and the first two embodiments is that the buffer solution is stuffed within the sampling part 21 in the third embodiment.

As FIG. 2 shows, the sampling part 21 is an extrusion tube, one end of the extrusion tube disposed the sampling loop 211, the opposite end of the extrusion tube disposed a sealed housing 212 stuffed with the buffer solution. The sealed housing may break through extruding the sealed housing 212, and release the buffer solution to mix with the liquid sample through the tube there between.

Although the locations of the buffer solution in mentioned two embodiments are different, the main character of the present invention is not affected, the present invention provides a quantitative sampling device which could perform quantitative sampling, dilution and isolation procedures with high efficiency, simple operation sequences and free of contamination.

To sum up, the quantitative sampling device disclosed herein provides a well tool for applying in POCT, it provides everyone to operate sample pretreatment procedures easily, and decrease the risk of contamination and analysis errors due by sampling un-quantitatively.

While the present invention has been particularly shown and described with reference to a preferred embodiment, it will be understood by those skilled in the art that various changes in form and detail may be without departing from the spirit and scope of the present invention.

We claim:

1. A quantitative sampling device comprising:
   a sampling part having a sampling loop with a predetermined size for sampling a fixed amount of a liquid sample;
   a case including a buffer solution with a predetermined volume;
   wherein the sampling part is adapted for slidable communication within the case, and the liquid sample may mix with the buffer solution to get a diluted solution.

2. The quantitative sampling device of claim 1 further comprising a filter membrane coupled to an opening end of the case for isolating the diluted solution to get a separated sample.

3. The quantitative sampling device of claim 2 further comprising an output part coupled to the filter membrane for outputting the separated sample.

4. The quantitative sampling device of claim 1, wherein the sampling part is a plunger having the sampling loop and a bar for propelling into the case.

5. A quantitative sampling apparatus comprising:
   a sampling part having a sampling loop with a predetermined size for sampling a fixed amount of a liquid sample, and including a buffer solution with a predetermined volume; and
   a case for receiving the sampling part and the buffer solution;
   wherein the sampling part is adapted for slidable communication within the case, and the liquid sample may mix with the buffer solution to get a diluted solution.

6. The quantitative sampling apparatus of claim 5 further comprising a filter membrane coupled to an opening end of the case for isolating the diluted solution to get an separated sample.

7. The quantitative sampling apparatus of claim 6 further comprising an output part coupled to the filter membrane for outputting the separated sample.

8. A pretreatment method of a liquid sample using a quantitative sampling device, the quantitative sampling device having a sampling part with a sampling loop, a buffer solution, a case, and a filter membrane, the method comprising:

quantitatively sampling the liquid sample through the sampling loop; propelling the sampling loop into the case; repeatedly mixing the buffer solution and the liquid sample to get a diluted solution; and propelling the sampling part to force the diluted solution passed through the filter membrane for isolating the diluted solution to get an separated sample.

9. The pretreatment method of claim 8, wherein the filter membrane sieves the passed solution according to pore sizes thereof.

\* \* \* \* \*